United States Patent [19]
Olsson et al.

[11] Patent Number: 5,522,381
[45] Date of Patent: Jun. 4, 1996

[54] DEVICE FOR SUPPLYING BREATHING GAS TO THE LUNGS OF A RESPIRATORY SUBJECT

[75] Inventors: Sven G. Olsson, Arloev; Goeran Rydgren, Bunkeflostrand; Anders Larsson, Kaevlinge, all of Sweden

[73] Assignee: Siemens-Elema AB, Solna, Sweden

[21] Appl. No.: 279,109

[22] Filed: Jul. 22, 1994

[30] Foreign Application Priority Data

Jul. 22, 1993 [SE] Sweden .................................. 9302477

[51] Int. Cl.$^6$ .................................................. A61M 15/00
[52] U.S. Cl. .................. 128/203.12; 128/203.25
[58] Field of Search ........................ 128/203.12, 203.25, 128/205.12, 205.19, 910, 911

[56] References Cited

U.S. PATENT DOCUMENTS

| | | | |
|---|---|---|---|
| 4,023,587 | 5/1977 | Dobritz | 128/203.25 |
| 4,265,239 | 5/1981 | Fischer, Jr. et al. | 128/910 |
| 4,312,339 | 1/1982 | Thompson, Sr. | 128/910 |
| 4,565,194 | 1/1986 | Weerda et al. | 128/205.19 |
| 4,617,924 | 10/1986 | Heim et al. | 128/204.23 |
| 4,702,242 | 10/1987 | Broddner et al. | 128/205.13 |
| 4,903,693 | 2/1990 | Yasue | 128/203.12 |
| 5,140,981 | 8/1992 | Lindstrom | 128/203.25 |

FOREIGN PATENT DOCUMENTS

| | | |
|---|---|---|
| 0166305 | 1/1986 | European Pat. Off. . |
| 545567 | 6/1993 | European Pat. Off. .............. 128/910 |
| 0570612 | 11/1993 | European Pat. Off. . |
| 9211887 | 7/1992 | WIPO .................................. 128/910 |

*Primary Examiner*—Aaron J. Lewis
*Attorney, Agent, or Firm*—Hill, Steadman & Simpson

[57] ABSTRACT

A device which supplies breathing gas mixed with an additive gas to a patient for pulmonary diagnosis or pulmonary treatment includes a gas mixing unit through which a relatively large flow of breathing gas is achieved from a first gas source through a first pressure regulator and a second pressure regulator. The breathing gas passes through a connecting tube from which the patient can breathe spontaneously through an inspiration tube, thereby inhaling air from the connecting tube. Expired gas passes via an expiration tube to the connecting tube. Additive gas is supplied from a separate gas source via a second pressure regulator and a second flow regulator. The additive gas is supplied in a flow which is considerably smaller than the flow of breathing gas, permitting a very small but accurate concentration of the additive gas to be achieved in the breathing gas. The large flow prevents a reactive additive gas from reacting before being supplied to the patient.

19 Claims, 2 Drawing Sheets

DEVICE FOR SUPPLYING BREATHING GAS TO THE LUNGS OF A RESPIRATORY SUBJECT

BACKGROUND OF THE INVENTION

1. Field of the Invention

The present invention relates to a device for supplying a breathing gas containing a predetermined concentration of a specific additive gas to the lungs of a respirating subject of the type having an inspiration tube through which breathing gas and additive gas are delivered to the lungs of the subject, an expiration tube through which expired gas is carried away from the lungs, a first adjustable gas source for supplying breathing gas to the inspiration tube and a second adjustable gas source for supplying at least the additive gas to the inspiration tube.

2. Description of the Prior Art

In the diagnosis of pulmonary function and treatment of the lungs, having a patient spontaneously breathe a breathing gas containing a predetermined concentration of a specific additive gas may be appropriate. The additive gas could be, e.g., nitric oxide (NO), nitrous oxide ($N_2O$), or sulphur hexafluoride ($SF_6$). For example, NO could be used for relaxing the smooth muscle cells in blood vessels and bronchi or for determining the diffusion capacity of the lungs. $N_2O$ could be used for determining the blood's rate of flow through the lungs, and $SF_6$ could be used for determining the functional residual capacity (FRC) of the lungs. Measurement of pulmonary pressure also supplies a measure of the resistance to flow through the lungs.

Certain additive gases, such as NO, react strongly with, e.g., oxygen and must therefore be added to breathing gas close to the patient so the additive gas is fed down into the lungs without having time to combine chemically with oxygen and form a toxic gas $NO_2$. In order to simplify the supplying of small amounts, such as one or two ppm, of an additive gas, the additive gas is usually mixed with some other gas, such as $N_2$, in a higher concentration, e.g. 100 ppm. This gas mixture is then added to the flow of breathing gas at a flow rate which is a predetermined fraction of the flow of breathing gas in order to produce the correct concentration. Gas is thus supplied in two stages.

European Application 0 570 612 describes a ventilator which can control very small flows. An accurate concentration of NO or some other additive gas can be delivered to a patient's lungs with such a ventilator, however, the ventilator is complex.

SUMMARY OF THE INVENTION

An object of the present invention is to provide a device which can supply a breathing gas containing a specific additive gas to the lungs, simply and reliably, in such a way that active additive gases do not have time to react with other gases before passing down into the lungs.

The object is achieved with a device in accordance with the invention wherein the first gas source supplies a continuous flow of the breathing gas, the second gas source supplies a continuous flow of the additive gas, a connecting tube is connected to the gas sources and a gas evacuation system, whereby the gas sources supply the breathing gas and the additive gas for mixing in the connecting tube, mixed gas passes through the connecting tube to the gas evacuation system, and the inspiration tube is connected to the connecting tube between the gas sources and the gas evacuation system, whereupon breathing gas and additive gas pass through the inspiration tube to the lungs at inhalation.

The continuous flow of breathing gas can advantageously be relatively large, e.g. 20 l/min. The additive gas, which could be, e.g. NO, diluted to 1000 ppm in $N_2$, is supplied at a slower flow rate, e.g. 20 ml/min up to 2 lmin. When additive gas is added to the breathing gas flow, the gases mix and result in a concentration of additive gas, NO in this instance, of e.g. 1 to 100 ppm. The continuous flow of mixed gas, however, must be at least as large as the patient's minute volume. When the patient inhales, gas in the connecting tube is drawn in through the inspiration tube to the lungs. Because of the large flow of gas, the additive gas does not have time to react with other gases before being drawn into the lungs. Relatively large flows are also easier to measure and control than small flows, so a desired concentration can therefore be attained by accurate control of flows. In principle, no gas meters are necessary. If the patient takes a breath so deep that the amount of gas supplied is inadequate, gas downstream from the inspiration tube's connection to the connecting tube is sucked back and passes into the inspiration tube. Thus, the connecting tube also serves as a reservoir for breathing gas and additive gas. This device also ensures that the patient always inspires a fresh gas mixture. Surplus additive gas which is not inspired by the patient is fed into the ambient atmosphere or into some type of collection vessel.

Preferably, the expiration tube in the device is connected to the connecting tube downstream from the location at which the inspiration tube is connected to the connecting tube. Only one gas evacuation system is then needed to dispose of both surplus gas and expired gas. Preferably, the connection between the expiration tube and the connecting tube is placed at distance far enough away from the connection between the inspiration tube and the connecting tube to prevent any expired air from being sucked up to the connection between the inspiration tube and the connecting tube.

A first gas meter can be connected to the inspiration tube in order to measure the concentration of additive gas. This would enhance patient safety. The gas meter could be connected to an alarm or to the second source of gas in order to reduce or cut off the flow of additive gas if that flow became too large. The gas meter could also be used in conjunction with various diagnostic investigations of the lungs.

In conjunction with both treatment and diagnostic examinations, it would be advantageous to provide a second gas meter connected to the expiration tube in order to measure the concentration of additive gas. The body's intake of additive gas can be determined when the concentration of both inspired and expired additive gas are measured. This measurement can also be performed, e.g., for determining the blood's rate of flow in the lungs by determining the body's intake of $N_2O$. The second gas meter can also be used, e.g., for determining the functional residual capacity (FRC) of the lungs.

The first source of gas may include a fan for generating the predetermined, continuous flow of breathing gas, whereby the breathing gas consists of ambient air.

The entire device can be made compact and suitable for treatment of patients at home or during transport when a fan is utilized to create the large flow of breathing gas.

Preferably, the additive gas is one of the gases NO, $N_2O$, $SF_6$ or an inert gas. These gases are well-known and used both in determinations of pulmonary function and in treatment of the lungs.

A gas mixture as disclosed in a co-pending application assigned to the same assignee as the present application, Ser. No. 08/279,108 (Gas Mixture and Device for Delivering the Gas Mixture to the Lungs of a Respirating Subject, Olsson et al), filed simultaneously herewith can also be used advantageously in the present device. As disclosed in that co-pending application, $SF_6$ is employed as a trace gas, whereby the concentration of the additive gas can be determined by using an exact mixture of $SF_6$ and additive gas in a known ratio and then measuring the concentration of $SF_6$. When a trace gas such as $SF_6$ is used, determining the concentration of the additive gas by measuring the concentration of trace gas on the expiration side of the device also becomes possible. The gas meter on the inspiration side then becomes unnecessary. The gas meters can also be calibrated before a patient is connected to the device by passing the desired mixture of breathing gas and additive gas through the gas meters. If an incorrect mixture is connected, the fault will be so large that even a non-calibrated gas meter will indicate that something is wrong. If the additive gas is an inert gas, the concentration of the trace gas measured must be corrected for the presence of inert gas in the atmosphere and thus in the breathing mixture.

DESCRIPTION OF THE PREFERRED EMBODIMENTS

Figure 1:
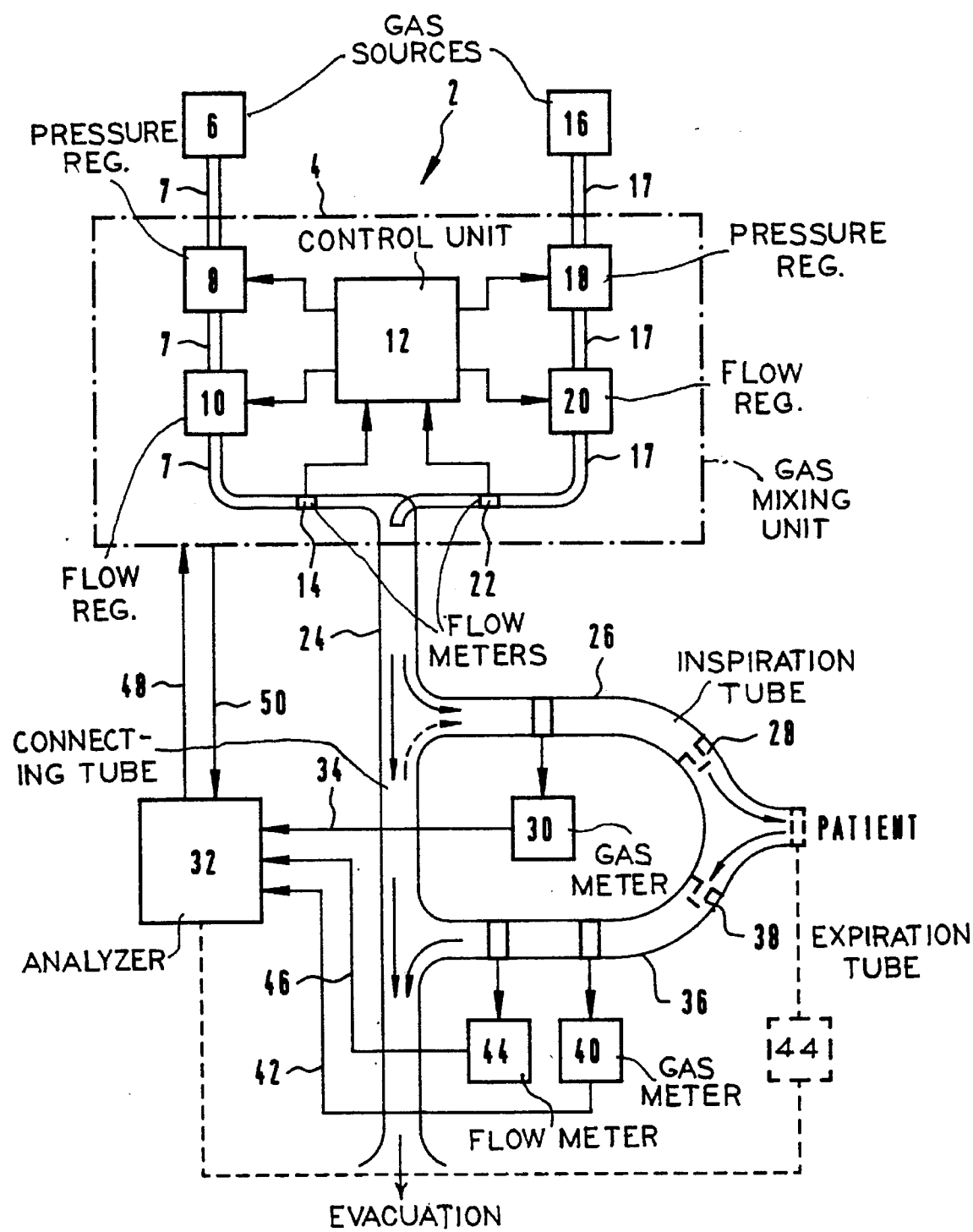
FIG. 1 shows a first embodiment of a device according to the invention.

The device 2 in FIG. 1 includes a gas mixing unit 4 which receives a breathing gas from a first gas source 6 via a gas tube 7. The breathing gas passes a first pressure regulator 8 and a first flow regulator 10 in order to achieve a predetermined pressure and flow which are controlled by a control unit 12. A first flow meter 14, which sends a measurement signal to the control unit 12, is also located in the gas tube 7. The control unit 12 then regulates the pressure regulator 8 and the flow regulator 10 on the basis of the measured flow.

The gas mixing unit 4 adds an additive gas from a second gas source 16 through, a gas tube 17. The additive gas passes a second pressure regulator 18 and a second flow regulator 20, both controlled by the control unit 12 on the basis of the flow measurement signals measured by a second flow meter 22. The additive gas could consist of, e.g., NO, diluted with $N_2$. A connecting tube 24 runs from the gas mixing unit 4 to a gas evacuation system. Breathing gas and the additive gas are mixed in the connecting tube 24. Breathing gas is added at a relatively large rate of flow, e.g., 20 l/min, whereas additive gas is added at a smaller rate of flow, e.g., 20 ml/min. With a predetermined concentration of 1000 ppm of NO in the second gas source 16, the gas in the connecting tube 24 will contain 1 ppm NO. The gas mixture passes from the connecting tube 24 in an inspiration tube 26 through a first check valve 28 to a patient who draws gas from the connecting tube 24 during spontaneous breathing, as indicated by an arrow in FIG. 1. If the patient takes a breath so deep that total flow is inadequate, gas is drawn downstream from the connection between the inspiration tube 26 and the connecting tube 24, as designated with a dashed arrow.

A first gas meter 30 for measuring the concentration of NO in the breathing gas is also located in the inspiration tube 26. The measurement value is sent to an analyzer 32 via a first signal line 34.

When the patient exhales, expired gas passes through the expiration tube 36 via a second check valve 38. In this way, the check valves 28 and 38 control the direction of flow through the inspiration tube 26 and the expiration tube 36. The expiration tube 36 then feeds to the connecting tube 24, and expired gas passes to the gas evacuation system with any surplus gas from the gas mixing unit 4. Evacuation can be into ambient air or a collection vessel of some type in which one or more different gases can be absorbed.

A second gas meter 40, which measures the concentration of NO in the expiration gas and sends a measurement signal to the analyzer 32 via a second signal line 42, is located in the expiration tube 36. The intake of NO in the body can determined, and thus the diffusion capacity of the lungs, can also be determined on the basis of the concentration of inspired NO and the concentration of expired NO.

A third flow meter 44 measures flow in the expiration tube 36 and sends the measurement value to the analyzer 32 via a third signal line 46. In addition to calculating diffusion capacity, the analyzer 32 can also include functions such as monitoring, alarm and control. The analyzer 32 can communicate with the gas mixing unit 4 via a fourth signal line 48 and a fifth signal line 50.

The third flow meter 44 can alternatively be located in the Y piece, as suggested in FIG. 1 with a dashed line. In this manner, the flow of both inspired and expired gas can be measured with a single flow meter.

Figure 2:
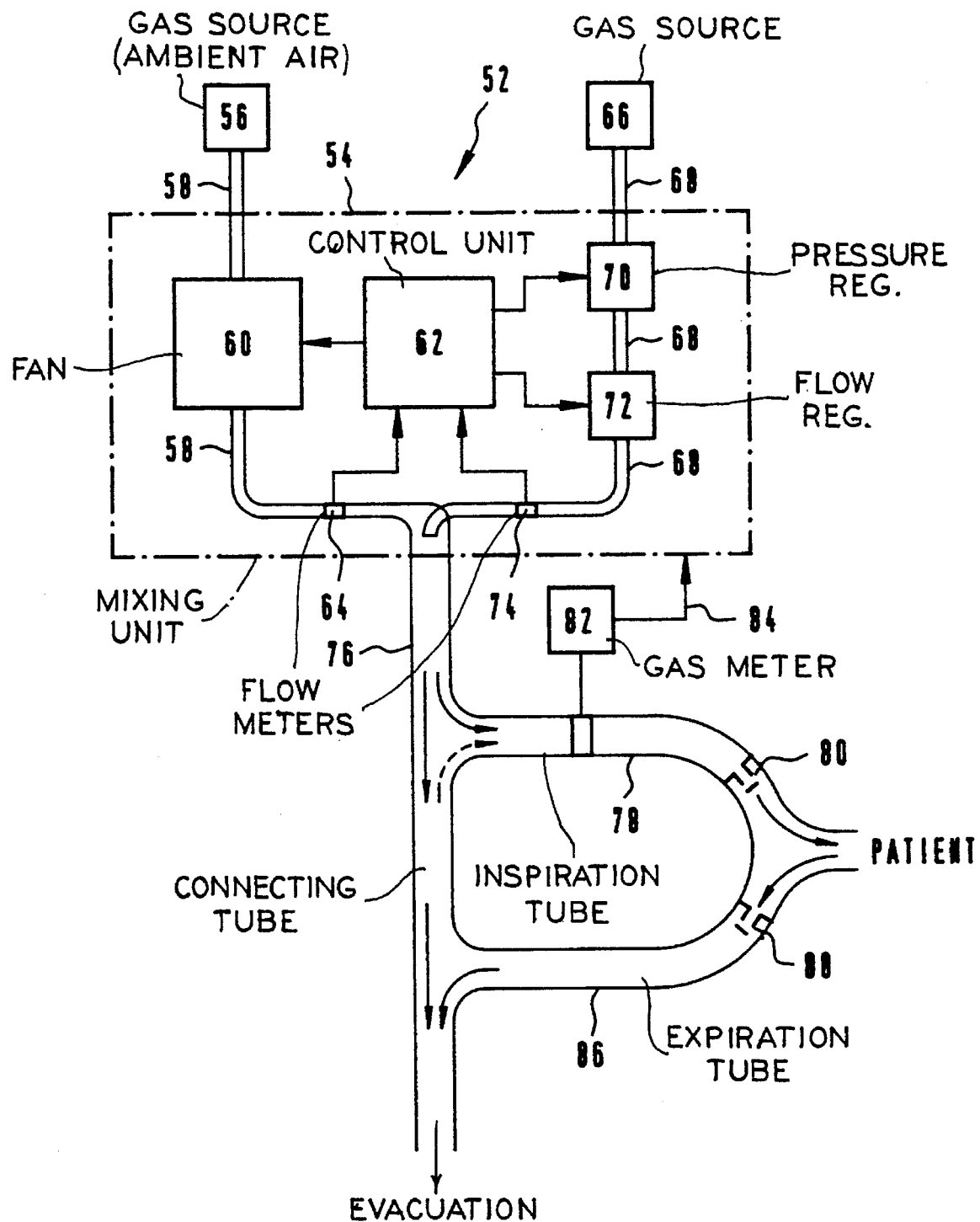
FIG. 2 shows a second embodiment of a device according to the invention.

FIG. 2 shows an alternative version of a device according to the invention. The device 52 has a gas mixing unit 54 supplied with a breathing gas from a first gas source 56 via a gas tube 58. In this instance, the first gas source 56 consists of ambient air, and the predetermined pressure and flow of breathing gas is generated by a fan 60. The fan is controlled by a control unit 62 on the basis of measurement signals from a first flow meter 64. An additive gas is supplied, as in the preceding embodiment, from a second gas source 66 through a gas tube 68 to a gas mixing unit 54. The additive gas passes a pressure regulator 70 and a flow regulator 72 so that a specific pressure and flow are attained. The pressure regulator 70 and the flow regulator 72 are controlled by the control unit 62 on the basis of measurement signals from a second flow meter 74.

The breathing gas and additive gas are mixed in a connecting tube 76 before passing through an inspiration tube 78 to a patient. As in the preceding instance, a first check valve 80 is located in the inspiration tube 78.

In this instance, a gas meter 82 measures the concentration of NO in inspiration gas and sends the measurement signal to the gas mixing unit 54 via a signal line 84. In this instance, treatment is intended for a patient with high vascular resistance in the pulmonary alveoli. A small amount of NO, less than 1 ppm, relaxes smooth muscle in the vessels, and the flow of blood increases past the alveoli.

Expiration gas passes from the patient via an expiration tube 86 through a second check valve 88 out to the connecting tube 76 and on to evacuation. As in the preceding instance, evacuation can be into ambient air or special collection vessels.

The invention is not limited to the described embodiments. Other gases, such as $SF_6$ and He, can be used for different diagnostic or therapeutic purposes. The device 52 according to the second embodiment can also include a gas meter and a flow meter on the expiration side and an analyzer for calculating various functions. In the corresponding manner, the device 2 according to the first embodiment can employ a fan for generating a flow of breathing gas from ambient air. Other combinations of the embodiments are also possible within the scope of the invention.

For example, the concentration of NO can be determined by adding an exact mixture of $SF_6$ and NO and measuring the concentration of $SF_6$. The $SF_6$ concentration then can be determined solely on the expiration side, whereby the flow of breathing gas can pass unimpeded to the patient.

In instances in which only a specific concentration of additive gas is to be supplied by the device, the device can be devised to supply a fixed flow from the respective gas source. The respective flow is periodically calibrated, and flows do not have to be measured or regulated. The device would thereby be simpler to make.

Even simpler regulation can be used if a somewhat less accurate concentration is permissible. For example, the large flow of breathing gas can be kept constant, and only the flow of additive gas is regulated. The simplest way to achieve this is by manual regulation. The NO concentration in the mixed gas can be determined for this purpose, e.g., by measurement of the trace gas $SF_6$ and used for regulation.

Providing the device with a plurality of gas sources and gas tubes to the connecting tube is also possible. For example, oxygen, air, $SF_6$ and NO can be supplied from four different gas sources and mixed in the connecting tube in the same way shown in the figures. One alternative is to supply oxygen from a separate source and using a fan which generates a flow of atmospheric air through the connecting tube.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for supplying breathing gas to the lungs of a respirating subject comprising:

a first adjustable gas source of breathing gas;

a second adjustable gas source of additive gas;

an inspiration tube and an expiration tube adapted for connection to said subject;

means for evacuating expired gas produced by said subject;

a connection tube leading from said first and second gas sources to said means for evacuating, to which each of said inspiration tube and said expiration tube are separately connected between said first and second gas sources and said means for evacuating; and means for supplying a constant flow of said breathing gas and said additive gas from said first and second gas sources in respective amounts to said connection tube for mixing in said connection tube to produce a gas mixture flowing through said connection tube to said means for evacuating expired gas, said gas mixture being inhaled by said subject from said connection tube through said inspiration tube and said expired gas being exhaled by said subject through said expiration tube.

2. A device as claimed in claim 1 wherein said expiration tube is connected to said connecting tube downstream from a location at which said inspiration tube is connected to said connecting tube.

3. A device as claimed in claim 1 further comprising: gas meter means connected in said inspiration tube for measuring a concentration of a said additive gas in said gas mixture inhaled by said subject.

4. A device as claimed in claim 1 further comprising gas meter means connected in said inspiration tube for measuring a concentration of said additive gas in said expiration gas.

5. A device as claimed in claim 1 wherein said first gas source comprises a fan for generating a predetermined, continuous flow of ambient air as said breathing gas.

6. A device as claimed in claim 1 wherein said second adjustable gas source comprises a second adjustable gas source containing additive gas selected from the group consisting of NO, $SF_6$, $N_2O$ and inert gases.

7. A device as claimed in claim 1 wherein said second adjustable gas source comprises a second adjustable gas source of additive gas consisting of a gas selected from the group consisting of NO, $N_2O$ and inert gases, and wherein said second adjustable gas source additionally contains $SF_6$ in a known ratio to said additive gas, wherein said inspiration tube and said expiration tube in combination comprise flow passages, and said device further comprising means disposed in said flow passes for measuring a concentration of $SF_6$ as a measurement of the concentration of said additive gas by means of said known ratio.

8. A device as claimed in claim 1 wherein said respirating subject has a minute volume associated therewith, and wherein said means for supplying a constant flow of said breathing gas and said additive gas comprises means for supplying a continuous flow of said mixed gas at least as large as said minute volume.

9. A device as claimed in claim 1 wherein said means for supplying a constant flow of said breathing gas and said additive gas comprises means for supplying a constant flow of said breathing gas which is significantly larger than said constant flow of said additive gas.

10. A device as claimed in claim 1 wherein said means for supplying a constant flow of said breathing gas and said additive gas comprises means for supplying a constant flow of approximately 20 l/min of said breathing gas and a constant flow of said additive gas in a range from approximately 20 ml/min.

11. A device for supplying breathing gas to the lungs of a respirating subject comprising:

a first adjustable gas source of breathing gas;

a second adjustable gas source of additive gas;

an inspiration tube adapted for connection to said subject;

an expiration tube adapted for connection to said subject for receiving expired gas from said subject;

means for evacuating gas;

a connection tube leading from said first and second gas sources to said means for evacuating gas, to which said inspiration tube is connected between said first and second gas sources and said means for evacuating gas; and means for supplying a constant flow of said breathing gas and said additive gas from said first and second gas sources in respective amounts to said connection tube for mixing in said connection tube to produce a gas mixture flowing through said connection tube to said means for evacuating gas, said gas mixture being inhaled by said subject from said connection tube through said inspiration tube and said expired gas being exhaled by said subject through said expiration tube.

12. A device as claimed in claim 11 further comprising: gas meter means connected in said inspiration tube for measuring a concentration of a said additive gas in said gas mixture inhaled by said subject.

13. A device as claimed in claim 11 further comprising gas meter means connected in said expiration tube for measuring a concentration of said additive gas in said expiration gas.

14. A device as claimed in claim 11 wherein said first gas source comprises a fan for generating a predetermined, continuous flow of ambient air as said breathing gas.

15. A device as claimed in claim 11 wherein said second adjustable gas source comprises a second adjustable gas source containing additive gas selected from the group consisting of NO, $SF_6$, $N_2O$ and inert gases.

16. A device as claimed in claim 11 wherein said second adjustable gas source comprises a second adjustable gas source of additive gas consisting of a gas selected from the group consisting of NO, $N_2O$ and inert gases, and wherein said second adjustable gas source additionally contains $SF_6$ in a known ratio to said additive gas, wherein said inspiration tube and said expiration tube in combination comprise flow passages, and said device further comprising means disposed in said flow passes for measuring a concentration of $SF_6$ as a measurement of the concentration of said additive gas by means of said known ratio.

17. A device as claimed in claim 11 wherein said respirating subject has a minute volume associated therewith, and wherein said means for supplying a constant flow of said breathing gas and said additive gas comprises means for supplying a continuous flow of said mixed gas at least as large as said minute volume.

18. A device as claimed in claim 11 wherein said means for supplying a constant flow of said breathing gas and said additive gas comprises means for supplying a constant flow of said breathing gas which is significantly larger than said constant flow of said additive gas.

19. A device as claimed in claim 11 wherein said means for supplying a constant flow of said breathing gas and said additive gas comprises means for supplying a constant flow of approximately 20 l/min of said breathing gas and a constant flow of said additive gas in a range from approximately 20 ml/min.

* * * * *